United States Patent
Takahashi et al.

(10) Patent No.: US 11,246,474 B2
(45) Date of Patent: Feb. 15, 2022

(54) FLEXIBLE TUBE INSERTION APPARATUS

(71) Applicant: OLYMPUS CORPORATION, Tokyo (JP)

(72) Inventors: Takeshi Takahashi, Hachioji (JP); Yuichi Ikeda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 495 days.

(21) Appl. No.: 16/182,676

(22) Filed: Nov. 7, 2018

(65) Prior Publication Data

US 2019/0082933 A1    Mar. 21, 2019

Related U.S. Application Data

(63) Continuation of application No. PCT/JP2016/068264, filed on Jun. 20, 2016.

(51) Int. Cl.
*A61B 1/005* (2006.01)
*A61B 1/00* (2006.01)
(Continued)

(52) U.S. Cl.
CPC ............ *A61B 1/0051* (2013.01); *A61B 1/00* (2013.01); *A61B 1/00006* (2013.01);
(Continued)

(58) Field of Classification Search
CPC ............ A61B 1/00004; A61B 1/00006; A61B 1/00039; A61B 1/00071; A61B 1/00078;
(Continued)

(56) References Cited

U.S. PATENT DOCUMENTS

2004/0059215 A1* 3/2004 Nishimura ............ G16H 15/00
                                                              600/410
2006/0217687 A1  9/2006 Bakos et al.
(Continued)

FOREIGN PATENT DOCUMENTS

JP      2006-263474 A    10/2006
JP        4656988 B2      3/2011
(Continued)

OTHER PUBLICATIONS

English translation of International Preliminary Report on Patentability dated Jan. 3, 2019 together with the Written Opinion received in related International Application No. PCT/JP2016/068264.
(Continued)

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

A insertion apparatus includes a flexible tube, a detection section that detects state information of the tube, a calculation section that calculates, based on the state information, shape information of the tube, and an input section that inputs characteristic information of the tube. The apparatus also includes a calculation section that calculates, based on the characteristic information, an operation state of a distal end of the tube, an calculation section that calculates an insertion state of the tube at a specific point closer to a proximal end than the distal end, based on the shape information, characteristic information, and operation state, and a measurement section that measures an actual operation state of the tube at the specific point.

8 Claims, 10 Drawing Sheets

(51) Int. Cl.
*A61B 1/01* (2006.01)
*A61B 1/273* (2006.01)
*A61B 1/31* (2006.01)

(52) U.S. Cl.
CPC ...... *A61B 1/00071* (2013.01); *A61B 1/00147* (2013.01); *A61B 1/01* (2013.01); *A61B 1/273* (2013.01); *A61B 1/31* (2013.01)

(58) Field of Classification Search
CPC ... A61B 1/00147; A61B 1/005; A61B 1/0051; A61B 1/0055; A61B 1/0056; A61B 1/01; A61B 1/273; A61B 1/31; A61B 1/0005; A61B 1/00055
See application file for complete search history.

(56) References Cited

U.S. PATENT DOCUMENTS

| | | | | |
|---|---|---|---|---|
| 2007/0038028 A1* | 2/2007 | Uchimura | ............ | A61B 1/0055 600/144 |
| 2010/0292566 A1* | 11/2010 | Nagano | ................ | A61B 5/6885 600/424 |
| 2011/0065991 A1* | 3/2011 | Sarvazyan | ............... | A61B 1/31 600/131 |
| 2013/0096423 A1* | 4/2013 | Yamamoto | ................ | A61B 1/01 600/424 |
| 2013/0109919 A1* | 5/2013 | Sugiyama | ............. | A61B 34/20 600/117 |
| 2013/0261392 A1* | 10/2013 | Yamamoto | ............ | A61B 1/0051 600/117 |
| 2014/0230562 A1* | 8/2014 | Yamamoto | ................ | G01N 3/20 73/800 |
| 2014/0330432 A1* | 11/2014 | Simaan | .................. | A61B 34/35 700/250 |
| 2015/0057575 A1* | 2/2015 | Tsusaka | ............. | A61B 1/00009 600/587 |
| 2015/0099926 A1* | 4/2015 | Davidson | ................ | A61B 34/20 600/103 |
| 2015/0313446 A1* | 11/2015 | Ogawa | ................. | A61B 1/0016 600/103 |
| 2015/0351608 A1* | 12/2015 | Choi | .................. | A61B 1/00045 600/103 |
| 2015/0359419 A1 | 12/2015 | Hane et al. | | |

FOREIGN PATENT DOCUMENTS

| | | |
|---|---|---|
| JP | 2016-007434 A | 1/2016 |
| WO | 2014/129436 A1 | 8/2014 |

OTHER PUBLICATIONS

International Search Report dated Sep. 13, 2016 issued in PCT/JP2016/068264.
English Abstract of corresponding JP 2006-288752 A dated Oct. 26, 2006.

* cited by examiner

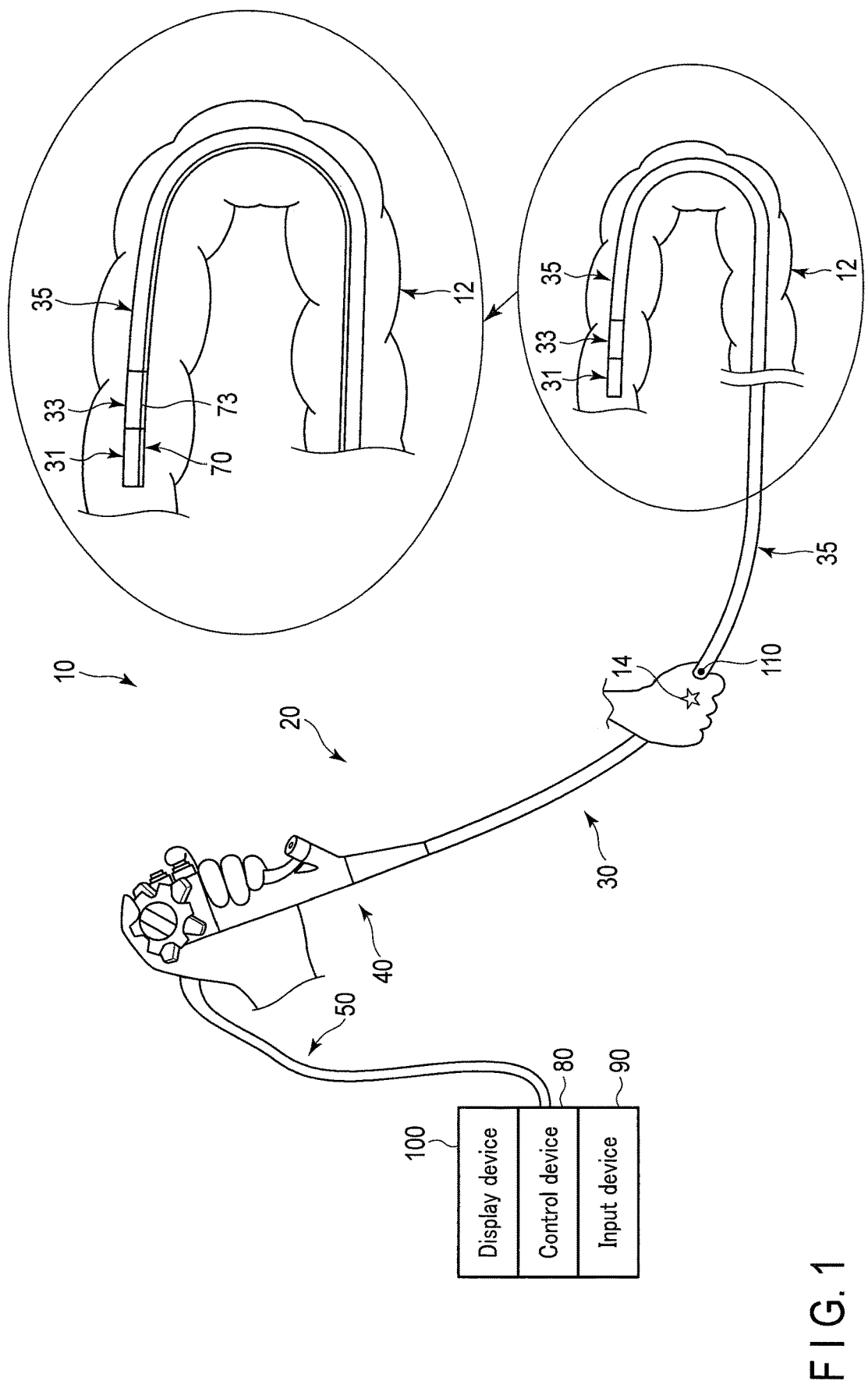
F I G. 1

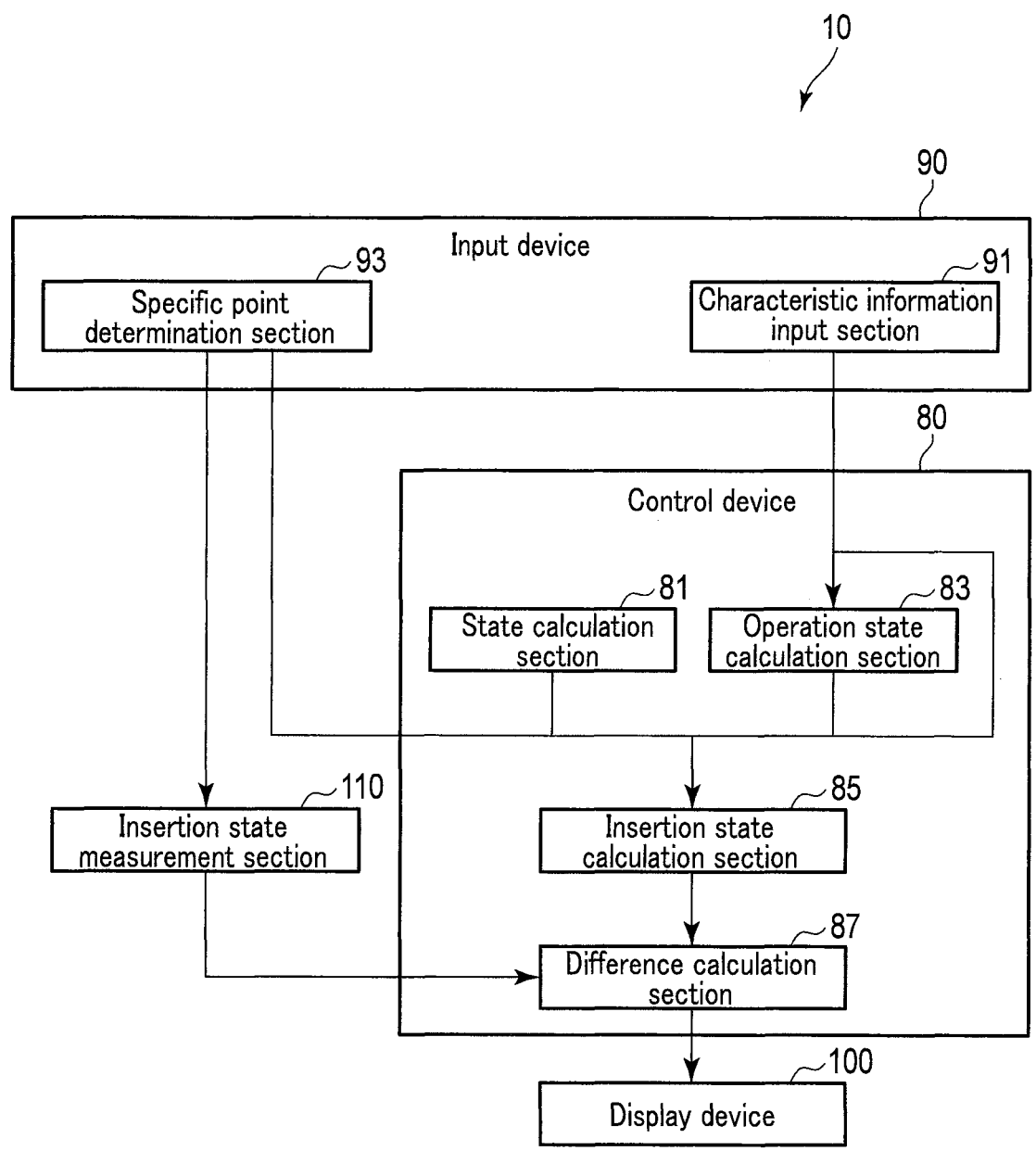
F I G. 2

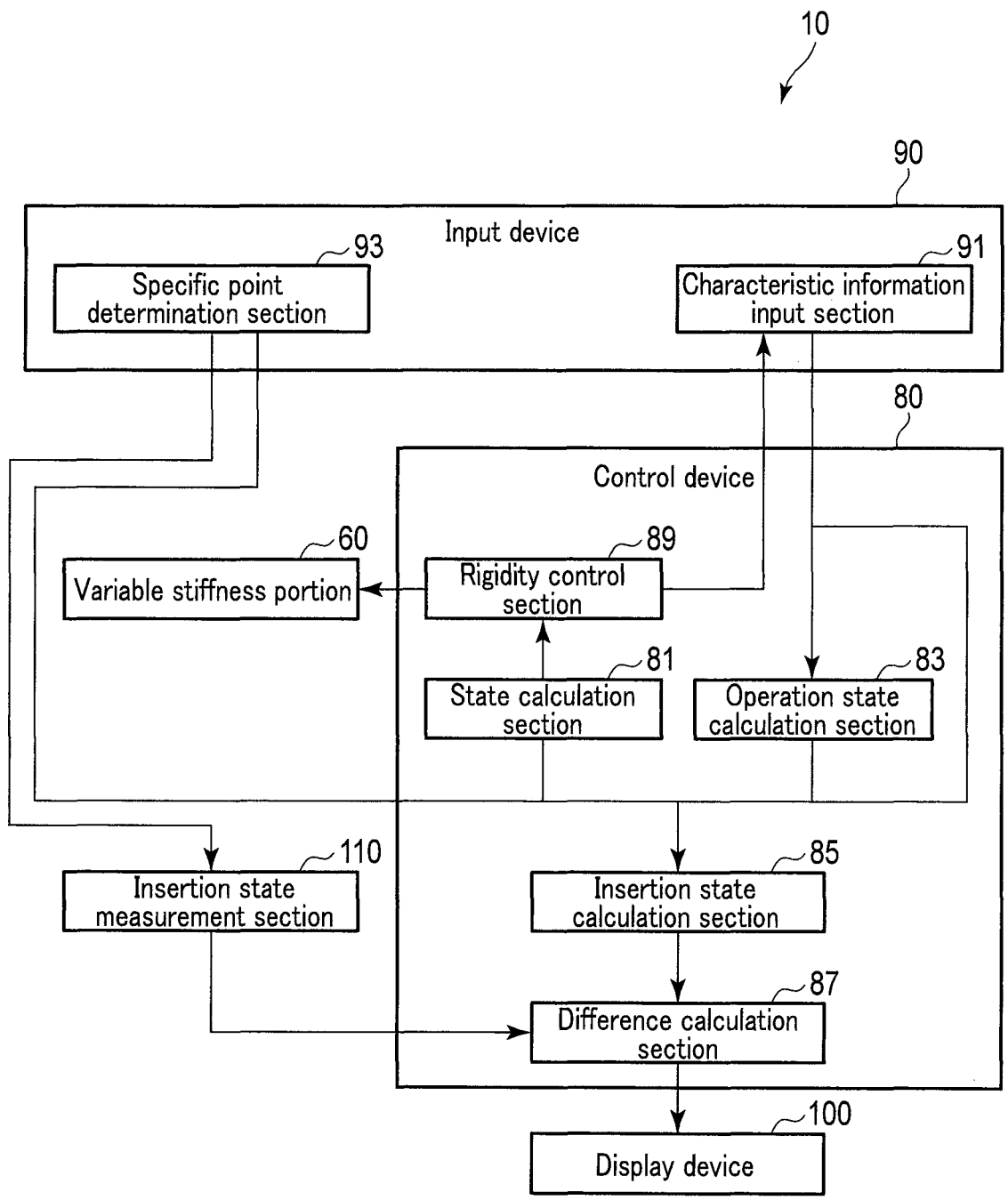
F I G. 10

FLEXIBLE TUBE INSERTION APPARATUS

CROSS-REFERENCE TO RELATED APPLICATIONS

This application is a Continuation Application of PCT Application No. PCT/JP2016/068264, filed Jun. 20, 2016, the entire contents of which are incorporated herein by reference.

BACKGROUND OF THE INVENTION

1. Field of the Invention

The present invention relates to a flexible tube insertion apparatus that inserts a flexible tube into a tube portion of a subject.

2. Description of the Related Art

When pushing a flexible, elongated insertion section of an endoscope forward into the inside of the intestine tract (tube portion) of the large intestine, an operator pushes the insertion section forward while gripping the proximal end side of the insertion section exposed to the outside from the anus. When a flexible, elongated insertion section is inserted into the intestine tract of the large intestine, the insertion section can be bent along the inner wall of the intestine tract of the large intestine. However, the sigmoid colon, the transverse colon, and the like are normally not fixed within the abdomen, and are easily moved inside the abdomen. Therefore, the intestinal tract is inevitably moved due to its high bendability and a push operation of the insertion section, so that the hand side force that pushes the insertion section forward may not be easily transmitted to the distal end of the insertion section. This is because the insertion section may be flexed in a direction different from the direction in which the insertion section is pushed forward, causing buckling that bends the insertion section in an unintended direction, for example.

An operator inserts the insertion section based on an image taken by the distal end of the insertion section or the sensation on the hand side during a push operation. At this time, if it is known which location the insertion section is inserted into in the tube portion, and what shape the insertion section forms, the insertability of the insertion section is improved. Accordingly, a shape detection device that detects a shape of the insertion section inserted into the tube portion has been developed.

However, an operator cannot determine from a shape of the insertion section detected by such a shape detection device, which location of the insertion section causes inhibition of insertion. In view of this, Japanese Patent No. 4656988, for example, discloses an endoscope insertion shape analysis apparatus configured to indicate which portion of the insertion section inhibits insertion or to indicate an inhibition factor portion so that based on indicated information, an operator can determine with accuracy what operation to take to deal with such inhibition.

BRIEF SUMMARY OF THE INVENTION

An aspect of the flexible tube insertion apparatus according to the present invention comprises: a flexible tube that is to be inserted into a subject; a state detection section that detects state information regarding a bending state of the flexible tube; a state calculation section that calculates, based on the state information, shape information regarding a shape of the flexible tube along a central axis direction of the flexible tube; a characteristic information input section that inputs characteristic information regarding a characteristic of the flexible tube; an operation state calculation section that calculates, based on the characteristic information, a distal end operation state indicative of an operation state of a distal end of the flexible tube; an insertion state calculation section that calculates a calculation insertion state indicative of an insertion state of the flexible tube at a specific point that is a predetermined point closer to a proximal end than the distal end in the flexible tube, based on the shape information, the characteristic information, and the distal end operation state.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of a flexible tube insertion apparatus according to a first embodiment of the present invention.

FIG. 2 is a diagram illustrating a relationship between a state calculation section, an operation state calculation section, an insertion state calculation section, a difference calculation section, a characteristic information input section, a specific point determination section, an insertion state measurement section, and a display device according to the first embodiment.

FIG. 10 is a diagram illustrating a relationship between a stiffness control section, a variable stiffness portion, a state calculation section, an operation state calculation section, an insertion state calculation section, a difference calculation section, a characteristic information input section, a specific point determination section, an insertion state measurement section, and a display device according to the second embodiment.

DETAILED DESCRIPTION OF THE INVENTION

Figure 3:
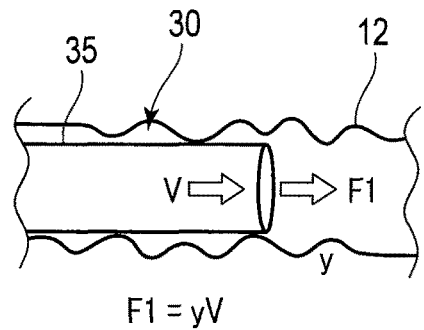
FIG. 3 is a diagram illustrating distal end insertion force F1.

Hereinafter, embodiments of the present invention will be explained in detail with reference to the accompanying drawings. In some of the drawings, illustration of some members is omitted for clarification of the illustration.

Hereinafter, the first embodiment of the present invention is described. As shown in FIG. 1, a flexible tube insertion apparatus (hereinafter, referred to as insertion apparatus 10) includes an endoscope 20, a control device 80 that controls the endoscope 20, an input device 90 that is connected to the control device 80, and a display device 100. The control device 80 functions as a control device that performs control in order to support the insertability of a flexible tube 35 of an insertion section 30 that is arranged in the endoscope 20. Although not shown, the insertion apparatus 10 may include a light source device that emits light for the endoscope 20 to observe and image.

The endoscope 20 will be explained as a medical flexible endoscope as an example, but is not limited thereto. The endoscope 20 is only required to include the flexible insertion section 30 to be inserted into a tube portion 12 (for example, the intestine tract of the large intestine) of a subject (for example, a patient), such as a flexible endoscope for an industrial use, a catheter, and a treatment instrument. The insertion section 30 is only required to include a site that has a flexibility so that the site can be flexed by an external force (for example, a flexible tube 35 to be described later). The endoscope 20 may be a front-viewing endoscope, or a side-viewing endoscope. A subject is not limited to, for example, a human, and may be an animal or any other structural object. The tube portion 12 may be, for example, a pipe for an industrial use.

The endoscope 20 includes the insertion section 30, a grip section 40 that is coupled to the proximal end of the insertion section 30 and is gripped by an operator of the insertion apparatus 10, and a universal cord 50 that extends from a side surface of the grip section 40. The universal cord 50 includes a connector that is detachably attachable to the control device 80.

The insertion section 30 is tubular, elongated, and flexible. The insertion section 30 advances toward and retreats from the tube portion 12 inside the tube portion 12. The insertion section 30 is bendable along a shape of the tube portion 12. The insertion section 30 includes a distal hard section 31, a bendable section 33, and the flexible tube 35 in this order from the distal end of the insertion section 30 toward the proximal end of the insertion section 30. The distal hard section 31 and the bendable section 33 are shorter than the flexible tube 35. Therefore, in the present embodiment, the distal hard section 31, the bendable section 33, and a distal end of the flexible tube 35 are deemed as a distal end of the insertion section 30. The flexible tube 35 has flexibility, and is flexed by an external force.

The insertion apparatus 10 includes the state detection section 70 that detects state information of the flexible tube 35 regarding a state of the flexible tube 35. The state information of the flexible tube 35 includes a bending state of the flexible tube 35. The bending state of the flexible tube 35 includes the bending quantity (the magnitude of bending) of the flexible tube 35, for example. The bending state of the flexible tube 35 may include a direction in which the flexible tube 35 is bent. The state information of the flexible tube 35 may include speed information. The speed information includes a magnitude and a direction of speed of the flexible tube 35 in the central axis direction of the flexible tube 35.

The state detection section 70 includes, for example, a fiber sensor that utilizes loss in the light transmission quantity caused by bending of an optical fiber 73. The fiber sensor includes a light source, not shown, which emits light, an optical fiber 73 that guides light, a reflector, not shown, that reflects light in a manner so that light guided by the optical fiber 73 proceeds reversely along the optical fiber 73, a light receiver, not shown, that receives reflected light, and a light branching unit, not shown. The light source includes, for example, an LED, etc. The light source is separate from a light source of the light source device, which emits light for observation and imaging. The optical fiber 73 is incorporated in the endoscope 20, and has flexibility. The optical fiber 73 has detection targets (not shown) that are mounted on the insertion section 30. The detection targets are arranged in mutually-different positions in the longitudinal axis direction of the optical fiber 73. The detection targets are only required to be arranged in sites in which the bending stiffness of the flexible tube 35 is to be changed. In the present embodiment, the detection targets are mutually arranged at equal intervals. The reflector is arranged in a distal end of the optical fiber 73 positioned in the distal end of the insertion section 30. The light receiver may include, for example, a spectroscopic element such as a spectroscope or a color filter, and a light receiving element such as a photodiode. The light source, the light receiver, and the proximal end of the optical fiber 73 are optically connected to the light branching unit. The light branching unit includes, for example, an optical coupler or a half mirror. The light branching unit guides light emitted from the light source to the optical fiber 73, and guides, to the light receiver, the return light having been reflected by the reflector and guided by the optical fiber 73. That is, light travels through the light source, the light branching unit, the optical fiber 73, the reflector, the optical fiber 73, the optical branching unit, and the light receiver in this order. The light source, the light receiver, and the light branching unit are mounted on the control device 80, for example.

When the insertion section 30 is bent, in accordance with the bend, the optical fiber 73 is bent. Accordingly, a part of light which propagates through the optical fiber 73 is emitted (leaked) to the outside through the detection targets having sensitivity in different wavelengths, for example. The detection targets are to change optical characteristics of the optical fiber 73, for example, the light transmission quantity of light with a predetermined wavelength. Therefore, when the optical fiber 73 is bent, the light transmission quantity of the optical fiber 73 is changed in accordance with the bending quantity of the optical fiber 73. An optical signal including information on this change in the light transmission quantity is received by the light receiver. The light receiver outputs the optical signal as state information of the flexible tube 35 to a state calculation section 81 (see FIG. 2) arranged in the control device 80.

Meanwhile, one detection target may be arranged in one optical fiber 73. In such a case, optical fibers are arranged. Assume that detection targets are arranged in the same position or close positions in the longitudinal axis direction of the optical fiber 73, and in positions mutually different around the axis of the longitudinal axis direction. In such a case, the bending quantity and the bending direction can be detected based on a combination of detection results by the plurality of detection targets.

The state detection section 70 includes a fiber sensor; however, this is not a limitation. The state detection section 70 may include, for example, any of a strain sensor, an acceleration sensor, a gyro sensor, and an element such as a coil. For example, the strain sensor detects bending strain caused by an external force (pressure) that the flexible tube 35 receives from the outside (for example, the tube portion 12). The acceleration sensor detects the acceleration of the flexible tube 35. The gyro sensor detects the angular speed of the flexible tube 35. The element generates a magnetic field in response to a state of the flexible tube 35, such as a shape of the flexible tube 35.

The state detection section 70 constantly performs detection (operation) after a detection start instruction is input from the input device 90 to the state detection section 70. The detection timing may be every predetermined elapse of time, and is not particularly limited.

The input device 90 is, for example, a general input device, and is, for example, a keyboard, a pointing device such as a mouse, a tag reader, a button switch, a slider, and a dial. The input device 90 may be used for an operator to input various instructions for operating the insertion apparatus 10.

Figure 6:
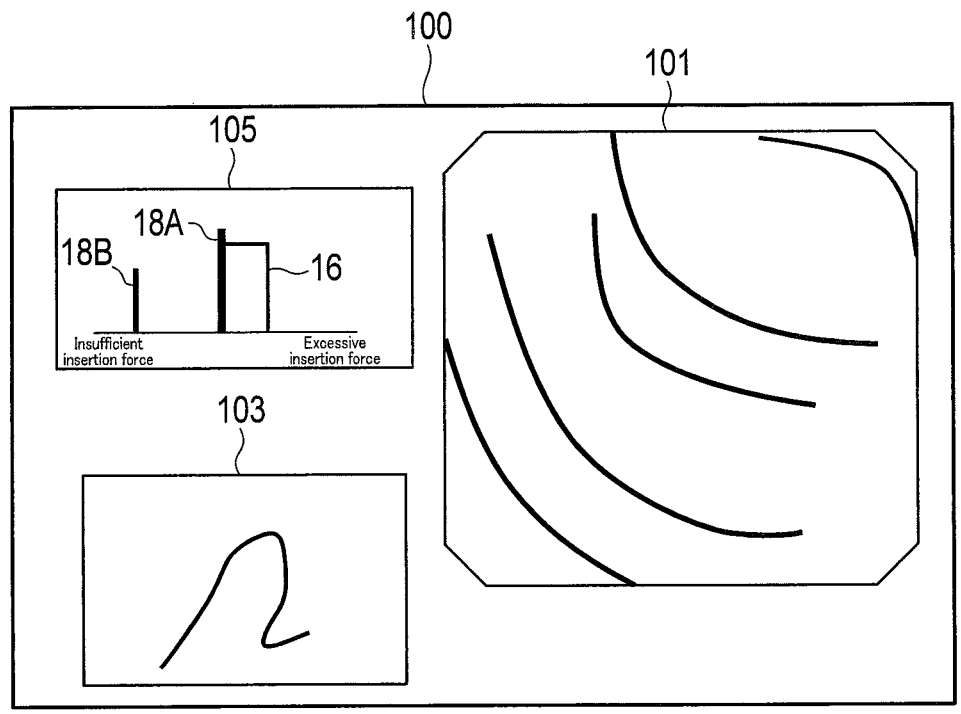
FIG. 6 is a diagram illustrating an example of a display on a display device.

As shown in FIG. 6, the display device 100 includes a first display 101 that displays an image taken by an imaging unit, not shown, a second display 103 that displays shape information of the flexible tube 35 calculated by the state calculation section 81 to be described later, and a third display 105 that displays at least the difference calculated by a difference calculation section 87 to be described later. The display device 100 includes, for example, a monitor. The imaging unit is incorporated in the insertion section 30, and includes, for example, a CCD, etc.

As shown in FIG. 2, the insertion apparatus 10 includes the state calculation section 81, an operation state calculation section 83, an insertion state calculation section 85, the difference calculation section 87, a characteristic information input section 91, a specific point determination section 93, and an insertion state measurement section 110. The state calculation section 81, the operation state calculation section 83, the insertion state calculation section 85, and the difference calculation section 87 are arranged in the control device 80. The characteristic information input section 91 and the specific point determination section 93 are arranged in the input device 90. A position in which the insertion state measurement section 110 is arranged will be described later.

The state calculation section 81, the operation state calculation section 83, the insertion state calculation section 85, and the difference calculation section 87 are configured by, for example, a hardware circuit including an ASIC and the like. At least one of the state calculation section 81, the operation state calculation section 83, the insertion state calculation section 85, and the difference calculation section 87 may be configured by a processor. In the case where at least one of those sections is configured by a processor, the internal memory or external memory, not shown, which is accessible by the processor, stores a program code that causes the processor to function as at least one of those sections when the processor is executed.

The state calculation section 81 calculates shape information regarding a shape of the flexible tube 35 along a central axis direction, based on the state information detected by the state detection section 70. For example, the state calculation section 81 calculates, at a predetermined time, shape information of the flexible tube 35 from a characteristic relation between light entering the optical fiber 73 and light exiting from the optical fiber 73. In detail, the state calculation section 81 calculates shape information based on state information output from the fiber sensor, specifically, a bending shape of a portion of the flexible tube 35, which is actually bent. This bending shape of the flexible tube 35 includes, for example, the bending quantity and the radius of curvature of the flexible tube 35. The state calculation section 81 may calculate the center direction of bending of the flexible tube 35, based on state information or shape information. The state calculation section 81 may calculate speed information as well as a shape. The state calculation section 81 outputs calculated shape information to the insertion state calculation section 85. The state calculation section 81 outputs calculated shape information to the display device 100, and the second display 103 displays the shape information as shown in FIG. 6. The state calculation section 81 may output calculated speed information to the display device 100, and the display device 100 may display the speed information.

The characteristic information input section 91 is, for example, a general input device, and is, for example, a keyboard and a pointing device such as a mouse. The characteristic information input section 91 inputs characteristic information regarding a characteristic of the flexible tube 35. The characteristic information includes at least viscous resistance y, bending stiffness K of the flexible tube 35, and coefficient μ of friction between a subject and the flexible tube 35. The characteristic information is a known value that is input through an operator's operation into the characteristic information input section 91. The characteristic information is input from the characteristic information input section 91 into the operation state calculation section 83 and the insertion state calculation section 85, through an operator's operation to the characteristic information input section 91. Therefore, the characteristic information input section 91 inputs the characteristic information into the operation state calculation section 83 and the insertion state calculation section 85, by an operation with respect to the characteristic information input section 91. The characteristic information input section 91 may be arranged in the control device 80 and may function as a storage that pre-stores characteristic information. For example, when the insertion apparatus 10 is activated, the characteristic information input section 91 may input pre-stored characteristic information into the operation state calculation section 83 and the insertion state calculation section 85. In detail, when the insertion apparatus 10 is activated, for example, the operation state calculation section 83 and the insertion state calculation section 85 may access the characteristic information input section 91 to read characteristic information.

The operation state calculation section 83 calculates, based on the characteristic information, a distal end operation state indicative of an operation state of the distal end of the flexible tube 35. The distal end operation state indicates, for example, the insertion force (hereinafter, referred to as distal end insertion force F1) at the distal end that causes the distal end of the flexible tube 35 to be inserted. That is, the distal end insertion force F1 corresponds to the force in the insertion direction of the flexible tube 35. The distal end insertion force F1 is calculated from the viscous resistance yin the characteristic information, as expressed in equation (3) to be described later. Meanwhile, the distal end operation state may indicate the speed at the distal end that causes the distal end of the flexible tube 35 to be inserted.

The specific point determination section 93 is, for example, a general input device, and is, for example, a keyboard and a pointing device such as a mouse. The specific point determination section 93 determines a specific point 14 (see FIG. 1) that is arranged on the central axis of the flexible tube 35. The specific point determination section 93 determines the specific point 14 by an operation with respect to the specific point determination section 93. The specific point determination section 93 inputs the determined specific point 14 to the insertion state calculation section 85 and the insertion state measurement section 110. The specific point 14 corresponds to a position presenting a site of the flexible tube 35, which is gripped by an operator, and also corresponds to a pushing position on the hand side on the central axis of the flexible tube 35. As shown in FIG. 1, the specific point determination section 93 may determine a position in which the insertion state measurement section 110 is arranged, as the specific point 14.

The insertion state calculation section 85 calculates a calculation insertion state indicative of an insertion state of the flexible tube 35 at the specific point 14 based on the shape information, the characteristic information, and the distal end operation state. For example, the shape information is about the bending quantity ΔR, the characteristic information is about the bending stiffness K and friction coefficient μ, and the distal end operation state is about distal end insertion force F1 or the speed at the distal end. The calculation insertion state is represented by a value that is calculated by analyzing respective numeric values of the bending quantity ΔR, the bending stiffness K, the friction coefficient μ, and the distal end operation state (insertion force or speed). If the distal end operation state corresponds to the distal end insertion force F1, the calculation insertion state corresponds to the insertion force in the insertion direction of the flexible tube 35 (hereinafter, referred to as the calculated insertion force). If the distal end operation state corresponds to a speed at the distal end, the calculation insertion state corresponds to a speed in the insertion direction of the flexible tube 35. As described, the calculation insertion state corresponds to the calculated insertion force or calculated speed at the specific point 14 in the insertion direction of the flexible tube 35. The insertion state calculation section 85 outputs the calculated calculation insertion state to the difference calculation section 87.

The insertion state measurement section 110 measures a measurement insertion state indicative of an actual operation state of the flexible tube 35 at the specific point 14 determined by the specific point determination section 93. The measurement insertion state is presented by a measured value that is directly measured by the insertion state measurement section 110. The measurement insertion state indicates the measured insertion force or measured speed at the specific point 14 in the insertion direction of the flexible tube 35. As shown in FIG. 1, the insertion state measurement section 110 is arranged in a site of the flexible tube 35, which is gripped by an operator. The insertion state measurement section 110 may be arranged in a glove, not shown, which covers a hand of an operator who grips the flexible tube 35. The insertion state measurement section 110 may be embedded in the flexible tube 35, for example. The insertion state measurement section 110 performs measurement in a position where it is arranged. The insertion state measurement section 110 includes any one of a force sensor, a torque sensor, a strain sensor, an acceleration sensor, and a position sensor. The insertion state measurement section 110 outputs a measured measurement insertion state to the difference calculation section 87.

The difference calculation section 87 compares the calculation insertion state with the measurement insertion state, to calculate a difference between the calculation insertion state and the measurement insertion state. The difference calculation section 87 outputs the calculation insertion state, the measurement insertion state, and the difference to the display device 100.

As shown in FIG. 6, the display device 100 displays, on the third display 105, at least the difference as support information for insertion of the flexible tube 35. The display device 100 displays, on the third display 105, the calculation insertion state, the measurement insertion state, and an appropriate range 16 as the support information. A display position of the measurement insertion state changes with respect to the calculation insertion state as a reference, based on the difference. Hereinafter, an example of a display will be described by using the calculation insertion force F3 as the insertion force in the calculation insertion state and the measurement insertion force F4 as the insertion force in the measurement insertion state. An index 18A indicative of the calculation insertion force F3 is fixed in terms of position, whereas an index 18B indicative of the measurement insertion force F4 is laterally shifted in the third display 105, depending on the difference. The difference corresponds to a difference between the calculation insertion force F3 and the measurement insertion force F4, and corresponds to a lateral distance between the index 18A and the index 18B in the third display 105. For example, as the difference is larger, the index 18B is arranged further away from the index 18A. For example, as the difference is smaller, the index 18B is arranged closer to the index 18A. As described above, the difference indicates a change in position of the index 18B with respect to the position of the index 18A in the third display 105, and indicates the change quantity of the measurement insertion force F4 with respect to the calculation insertion force F3. The display device 100 displays whether the measurement insertion state is insufficient or excessive relative to the calculation insertion state, and whether the measurement insertion state falls within the appropriate range 16 or outside the appropriate range 16.

The appropriate range 16 is set as desired by the input device 90, and is input to the display device 100. The appropriate range 16 may be stored in a storage, not shown. The appropriate range 16 is set as desired depending on a subject. Hereinafter, the appropriate range 16 will be described by using the calculation insertion force F3 and the measurement insertion force F4. When the measurement insertion force F4 is applied to the flexible tube 35, it is transmitted to the distal end of the flexible tube 35. In this respect, the appropriate range 16 is a range that indicates whether the insertion quantity is optimal for insertion of the distal end of the flexible tube 35 toward a deep portion. The lower limit of this range corresponds to the calculation insertion force F3. When the measurement insertion force F4 is insufficient relative to the calculation insertion force F3, the measurement insertion force F4 is not transmitted to the distal end of the flexible tube 35, so that the distal end of the flexible tube 35 is not inserted toward a deep portion. When the measurement insertion force F4 is excessive relative to the appropriate range 16, buckling is caused in which the flexible tube 35 is flexed in a direction different from the insertion, or is bent in an unintended direction, for example.

The display device 100 functions as a supply device that supplies support information through display. Although the display device 100 is described as an example of the supply device, the supply device is not necessarily limited to this, and support information may be supplied by means of sound or may be projected on a screen, not shown. The supply device may function as a wearable terminal of a spectacle type or a head-mounted display type, which is removably wearable for an operator.

Hereinafter, an example of operation of the insertion apparatus 10 will be explained. As an example of the distal end operation state, the calculation insertion state, and the measurement insertion state, the description is made using the insertion force. However, these states are not necessarily limited to the insertion force, and may be a speed.

When inserting the flexible tube 35 into a deep portion in the tube portion 12, an operator pushes the flexible tube 35 from a hand side. As shown in FIG. 3, the distal end insertion force F1 in the distal end in which the distal end of the flexible tube 35 is inserted is generally determined by, for example, the speed V of the distal end, and the viscous resistance y between the distal end of the flexible tube 35 and a target, and is expressed by equation (1) below.

$$F1=y \times V \qquad \text{Equation (1)}$$

Equation (1) is expressed by equation (2) below.

$$V=F1/y \qquad \text{Equation (2)}$$

The flexible tube 35 being inserted indicates V>0. Therefore, the distal end insertion force F1 is only required to exceed the viscous resistance y, and equation (3) is presented.

$$F1>y \qquad \text{Equation (3)}$$

The viscous resistance y is a known value that is input as characteristic information by the characteristic information input section 91. Therefore, the distal end insertion force F1 is calculated by the operation state calculation section 83, as a value greater than or equal to the viscous resistance y.

Figure 4:
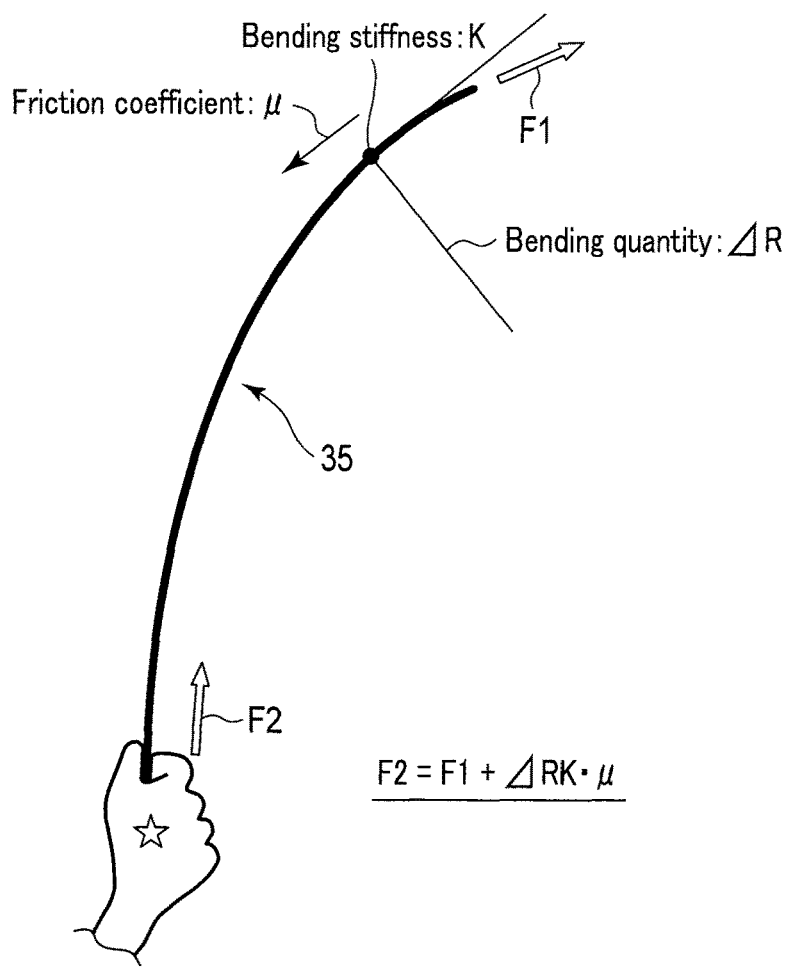
FIG. 4 is a diagram illustrating hand side insertion force F2.

As shown in FIG. 4, the insertion force in an arbitrary point on the central axis of the flexible tube 35 is referred to as hand side insertion force F2. An arbitrary point indicates a hand side such as the specific point 14, for example. The hand side insertion force F2 is calculated by the insertion state calculation section 85, based on the bending quantity ΔR as the shape information calculated by the state calculation section 81, the bending stiffness K and the friction coefficient μ as the characteristic information input by the characteristic information input section 91, and the distal end insertion force F1 calculated by the operation state calculation section 83. The hand side insertion force F2 is expressed by equation (4) below. The bending stiffness K and the friction coefficient μ take known values that are input as the characteristic information by the characteristic information input section 91.

$$F2-\Delta RK \cdot \mu = F1 \qquad \text{Equation (4)}$$

ΔRK represents a force of shape loss.

Equation (4) is expressed by equation (5) below.

$$F2=F1+\Delta RK \cdot \mu \qquad \text{Equation (5)}$$

That is, it is understood that the hand side insertion force F2 can be calculated by the insertion state calculation section 85, based on equation (5).

Figure 5:
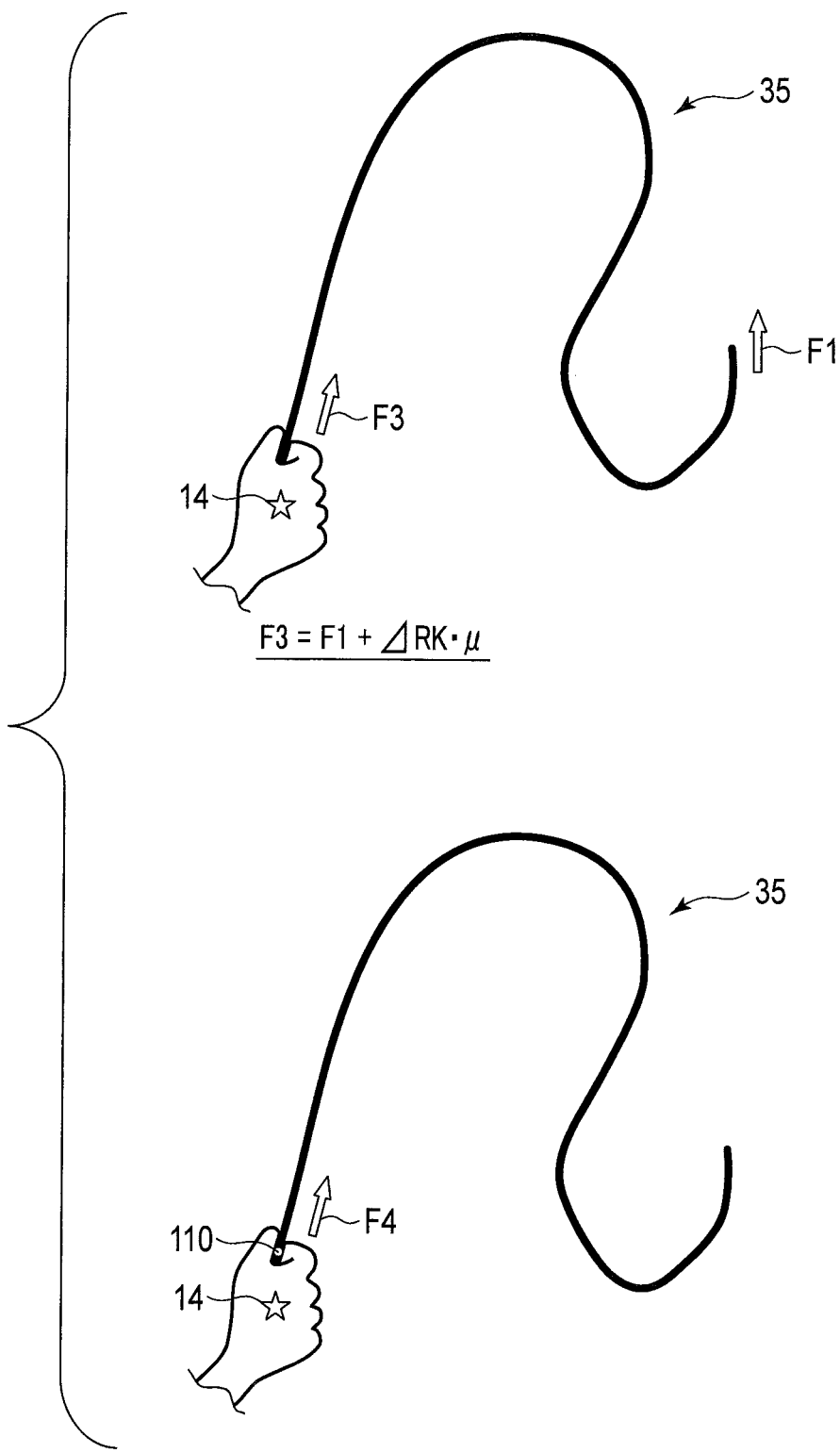
FIG. 5 is a diagram illustrating calculation insertion force F3 and measurement insertion force F4.

Herein, as shown in FIG. 5, an arbitrary point is referred to as the specific point 14 that is determined by the specific point determination section 93. The calculation insertion force F3 at the specific point 14, which is determined by the insertion state calculation section 85, is expressed as equation (6) based on equation (5).

$$F3=F1+\Delta RK \cdot \mu \qquad \text{Equation (6)}$$

The calculation insertion force F3 takes a value that is calculated based on the distal end insertion force F1 and a known value, and can be regarded as the insertion force on the distal end side. The calculation insertion force F3 is output from the insertion state calculation section 85 and is input to the difference calculation section 87.

As shown in FIG. 5, the insertion state measurement section 110 measures the measurement insertion force F4 at the specific point 14. The measurement insertion force F4 corresponds to the measured hand side insertion force.

The insertion state measurement section 110 measures the measurement insertion force F4 at a timing when the insertion state calculation section 85 calculates the calculation insertion force F3. The insertion state measurement section 110 measures the measurement insertion force F4 with respect to the shape of the flexible tube 35 in which the calculation insertion force F3 has been calculated by the insertion state calculation section 85. That is, the calculation insertion force F3 and the measurement insertion force F4 are calculated and measured at the same timing with respect to the same shape.

The difference calculation section 87 compares the calculation insertion force F3 with the measurement insertion force F4, and calculates the difference of the measurement insertion force F4 with respect to the calculation insertion force F3. As shown in FIG. 6, the calculation insertion force F3, the measurement insertion force F4, the difference, and the appropriate range 16 are visually displayed by the third display 105 of the display device 100.

As an example of display, as shown in FIGS. 7A, 7B, 7C, and 7D, the index 18A indicative of the calculation insertion force F3 is displayed as a central axis defined as a vertical axis, whereas the index 18B indicative of the measurement insertion force F4 is displayed as a vertical axis that is shifted with respect to the index 18A in accordance with the difference. As shown in FIGS. 8A, 8B, 8C, and 8D, the index 18B indicative of the measurement insertion force F4 may be displayed as a horizontal bar that is extensible in accordance with the difference with respect to the index 18A indicative of the calculation insertion force F3. The difference corresponds to a distance between the index 18A and the index 18B. The appropriate range 16 corresponds to a region on the side of excess with respect to the calculation insertion force F3.

Figure 7A:
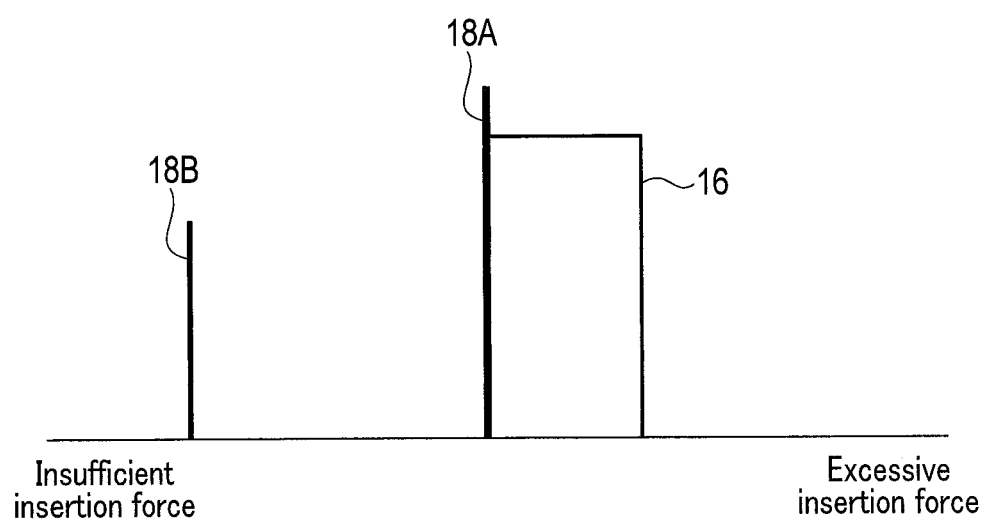
FIG. 7A is a diagram illustrating an example of the display indicating that the measurement insertion force F4 is largely insufficient relative to the calculation insertion force F3.
Figure 7B:
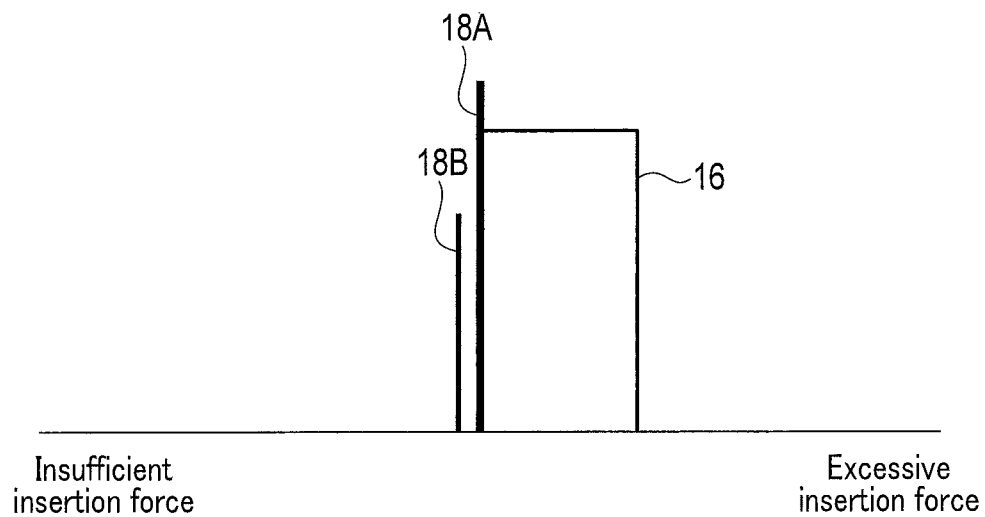
FIG. 7B is a diagram illustrating an example of the display indicating that the measurement insertion force F4 is slightly insufficient relative to the calculation insertion force F3.
Figure 7C:
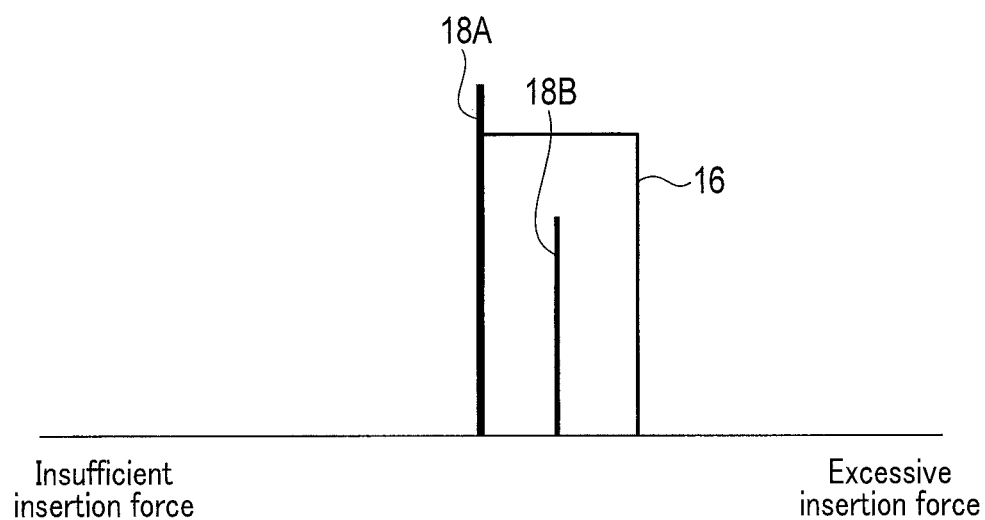
FIG. 7C is a diagram illustrating an example of the display indicating that the measurement insertion force F4 is an appropriate insertion force with respect to insertion.
Figure 7D:
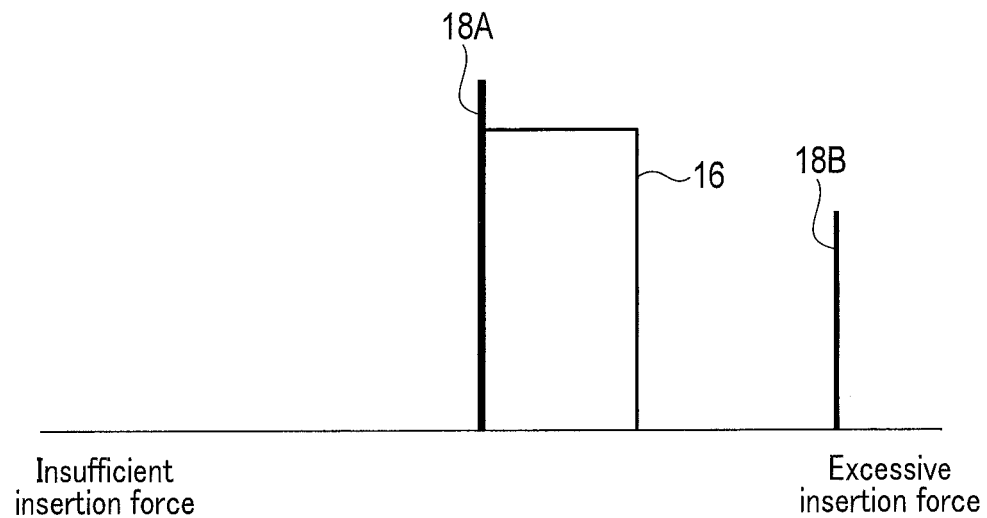
FIG. 7D is a diagram illustrating an example of the display indicating that the measurement insertion force F4 is largely excessive relative to the calculation insertion force F3.
Figure 8A:
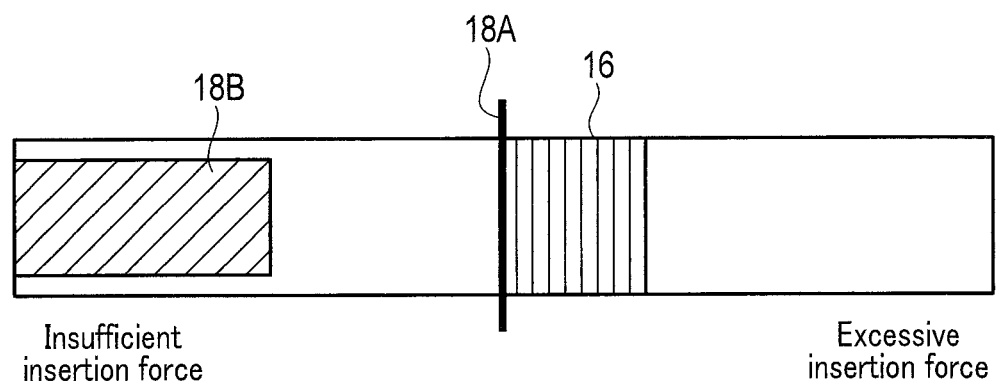
FIG. 8A is a diagram illustrating an example of the display indicating that the measurement insertion force F4 is largely insufficient relative to the calculation insertion force F3.
Figure 8B:
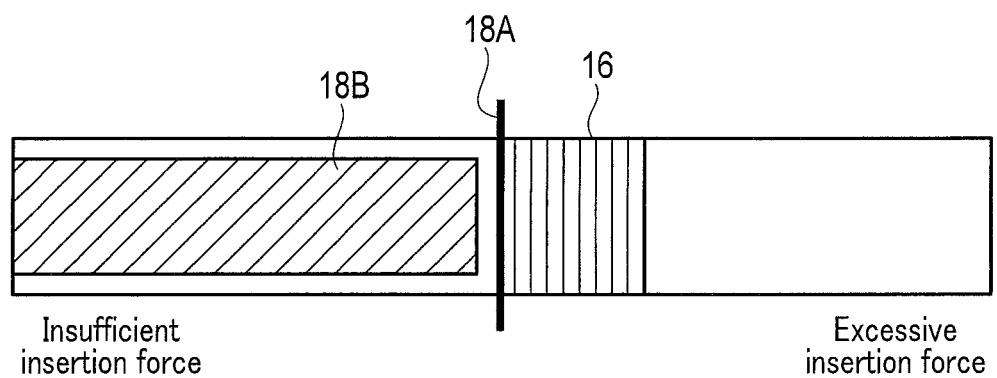
FIG. 8B is a diagram illustrating an example of the display indicating that the measurement insertion force F4 is slightly insufficient relative to the calculation insertion force F3.
Figure 8C:
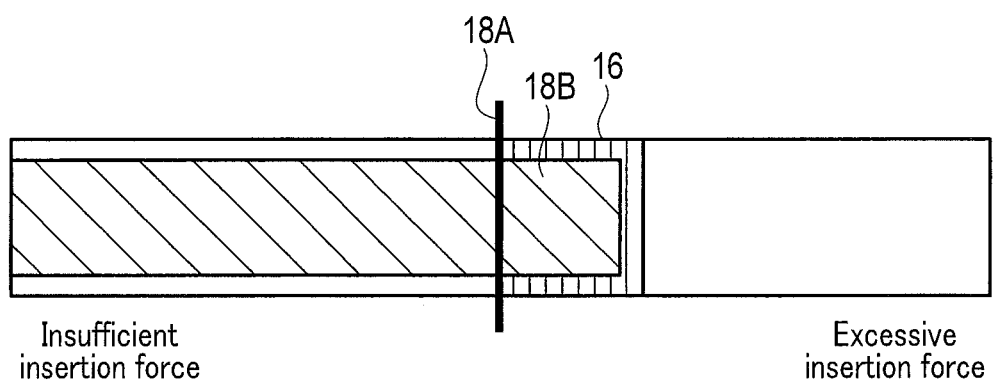
FIG. 8C is a diagram illustrating an example of the display indicating that the measurement insertion force F4 is an appropriate insertion force with respect to insertion.

The index 18B indicative of the measurement insertion force F4 as the insertion force on the hand side, shown in FIGS. 7A and 8A, is largely insufficient relative to the index 18A indicative of the calculation insertion force F3 as the insertion force on the distal end side. The index 18B indicative of the measurement insertion force F4 shown in FIGS. 7B and 8B, is increased compared to the index 18B indicative of the measurement insertion force F4 shown in FIGS. 7A and 8A, but is slightly insufficient relative to the index 18A indicative of the calculation insertion force F3. The index 18B indicative of the measurement insertion force F4 shown in FIGS. 7C and 8C is increased compared to the index 18B indicative of the measurement insertion force F4 shown in FIGS. 7B and 8B, and presents the insertion force appropriate for the insertion falling within the appropriate range 16. The index 18B indicative of the measurement insertion force F4 shown in FIGS. 7D and 8D is increased compared to the index 18B indicative of the measurement insertion force F4 shown in FIGS. 7C and 8C, is excessive relative to the index 18A indicative of the calculation insertion force F3, and presents the insertion force beyond the appropriate range 16.

In the conditions shown in FIGS. 7A, 7B, 8A, and 8B, the measurement insertion force F4 is insufficient relative to the calculation insertion force F3. Thus, even when the measurement insertion force F4 on the hand side is applied to the flexible tube 35, the measurement insertion force F4 is not transmitted to the distal end of the flexible tube 35, so that the distal end of the flexible tube 35 is not inserted toward a deep portion. In the condition shown in FIGS. 7C and 8C, the measurement insertion force F4 falls within the appropriate range 16 with respect to the calculation insertion force F3. Thus, the measurement insertion force F4 is transmitted to the distal end of the flexible tube 35, so that the distal end of the flexible tube 35 is inserted. In other words, the measurement insertion force F4 has reached the calculation insertion force F3 necessary for the insertion of the distal end of the flexible tube 35. In the condition shown in FIGS. 7D and 8D, the measurement insertion force F4 is excessive relative to the calculation insertion force F3. Thus, when the measurement insertion force is applied to the flexible tube 35, buckling is caused in which the flexible tube 35 is flexed in a direction different from the insertion, or is bent in an unintended direction. This causes distress to a patient.

Figure 8D:
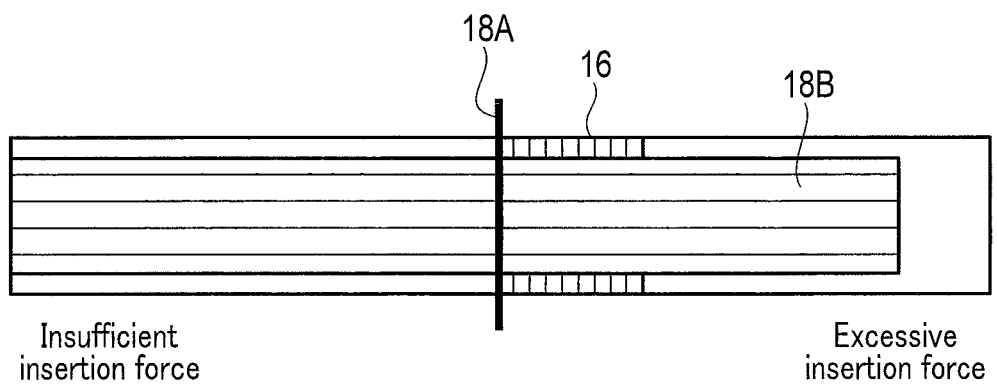
FIG. 8D is a diagram illustrating an example of the display indicating that the measurement insertion force F4 is largely excessive relative to the calculation insertion force F3.

As shown in FIGS. 8A, 8B, 8C, and 8D, a color used for display of the index 18B may be changed in accordance with the growth of the index 18B indicative of the measurement insertion force F4 relative to the index 18A indicative of the calculation insertion force F3. For example, as shown in FIGS. 8A and 8B, if the measurement insertion force F4 is insufficient relative to the calculation insertion force F3, the index 18B is displayed in green. As shown in FIG. 8C, if the measurement insertion force F4 is the insertion force within the appropriate range 16 with respect to the calculation insertion force F3, the index 18B is displayed in blue. As shown in FIG. 8D, if the measurement insertion force F4 is excessive relative to the calculation insertion force F3, the index 18B is displayed in red.

In an insertion operation in progress, an operator visually observes the index 18A indicative of the calculation insertion force F3, the index 18B indicative of the measurement insertion force F4, and the appropriate range 16, all of which are display contents displayed on the display device 100, and determines whether the measurement insertion force F4 is insufficient, excessive, or appropriate. In other words, a display content functions as support information that supports the insertion into a deep portion in the tube portion 12. Therefore, an operator visually observes support information and based on the support information, adjusts the measurement insertion force F4. In other words, the insertion apparatus 10 supports the insertion of the flexible tube 35 into a deep portion in the tube portion 12, with the help of the support information.

When the index 18B indicative of the measurement insertion force F4 falls within the appropriate range 16, the measurement insertion force F4 is transmitted to the distal end of the flexible tube 35, so that the distal end of the flexible tube 35 is inserted toward a deep portion. Thus, the insertability is improved. In addition, since this is not an excessive pushing operation, the flexible tube 35 does not apply any excessive load unintentionally to the large intestine wall, for example. Thus, the patient's distress is reduced.

In the present embodiment, the difference calculation section 87 compares the calculation insertion state with the measurement insertion state, thereby calculating the difference between the calculation insertion state and the measurement insertion state. The display device 100 displays and supplies at least the difference as support information. Therefore, according to the present embodiment, the insertion into a deep portion in the tube portion 12 can be supported with the help of the support information. As a result, according to the present embodiment, it is possible to prevent the flexible tube 35 from buckling and to improve the insertability into a deep portion in the tube portion 12, so that a load to a subject, such as patient distress, can be reduced without giving any excessive load unintentionally to the wall part of the tube portion 12. The display device 100 displays and supplies the calculation insertion state, the measurement insertion state, and the appropriate range 16, all of which are support information. Therefore, according to the present embodiment, the insertion into a deep portion in the tube portion 12 can be reliably supported by means of the support information.

According to the present embodiment, a display position of the measurement insertion state changes with respect to the calculation insertion state, based on the difference. Furthermore, the display device 100 displays whether the measurement insertion state is insufficient or excessive relative to the calculation insertion state, and whether the measurement insertion state falls within the appropriate range 16 or outside the appropriate range 16. Therefore, in an insertion operation in progress, an operator can easily ascertain support information by visually observing display contents displayed on the display device 100. Based on the ascertained support information, an operator can easily adjust the measurement insertion force F4. In other words, the insertion apparatus 10 can support the insertion of the flexible tube 35 into a deep portion inside the tube portion 12 by means of the support information.

According to the present embodiment, the characteristic information includes the viscous resistance y, the bending stiffness K of the flexible tube, the coefficient µ of friction between a subject and the flexible tube, and a value of viscoelasticity, and they are represented as known values. Therefore, according to the present embodiment, the distal end operation state and the calculation insertion state can be easily calculated.

In the present embodiment, the characteristic information input section 91 inputs the characteristic information. Therefore, according to the present embodiment, the distal end operation state and the calculation insertion state can be easily calculated. According to the present embodiment, the characteristic information input section 91 inputs the characteristic information to the operation state calculation section 83 and the insertion state calculation section 85, by an operator's operation to the characteristic information input section 91. This enables the calculation of the optimum distal end operation state and calculation insertion state in accordance with the tube portion 12. Alternatively, when the insertion apparatus 10 is activated, the characteristic information input section 91 that functions as a storage inputs the characteristic information pre-stored therein to the operation state calculation section 83 and the insertion state calculation section 85. This enables the immediate calculation of the distal end operation state and the calculation insertion state.

According to the present embodiment, the specific point determination section 93 determines the specific point 14 by the operator's operation to the specific point determination section 93. Thus, a desired position can be set to the specific point 14. The specific point determination section 93 determines, as the specific point 14, a position in which the insertion state measurement section 110 is arranged. This saves the effort of determining the specific point 14.

In the present embodiment, the calculation insertion state indicates the insertion force or speed, whereas the measurement insertion state indicates the insertion force or speed. The parameter of the calculation insertion state is the same as the parameter of the measurement insertion state. That is, if the calculation insertion state corresponds to the insertion force, the calculation insertion state corresponds to the insertion force. If the calculation insertion state corresponds to the speed, the measurement insertion state corresponds to the speed. Therefore, a parameter such as the insertion force or speed can be supplied as support information that can be easily ascertained by an operator.

According to the present embodiment, the insertion state measurement section 110 is a force sensor or the like, which can reduce the cost and provide a simple structure.

Hereinafter, a second embodiment of the present invention will be described. In the present embodiment, only the features different from those of the first embodiment will be described.

The control device 80 functions as a stiffness control device that controls the bending stiffness of the flexible tube 35, for example.

Figure 9:
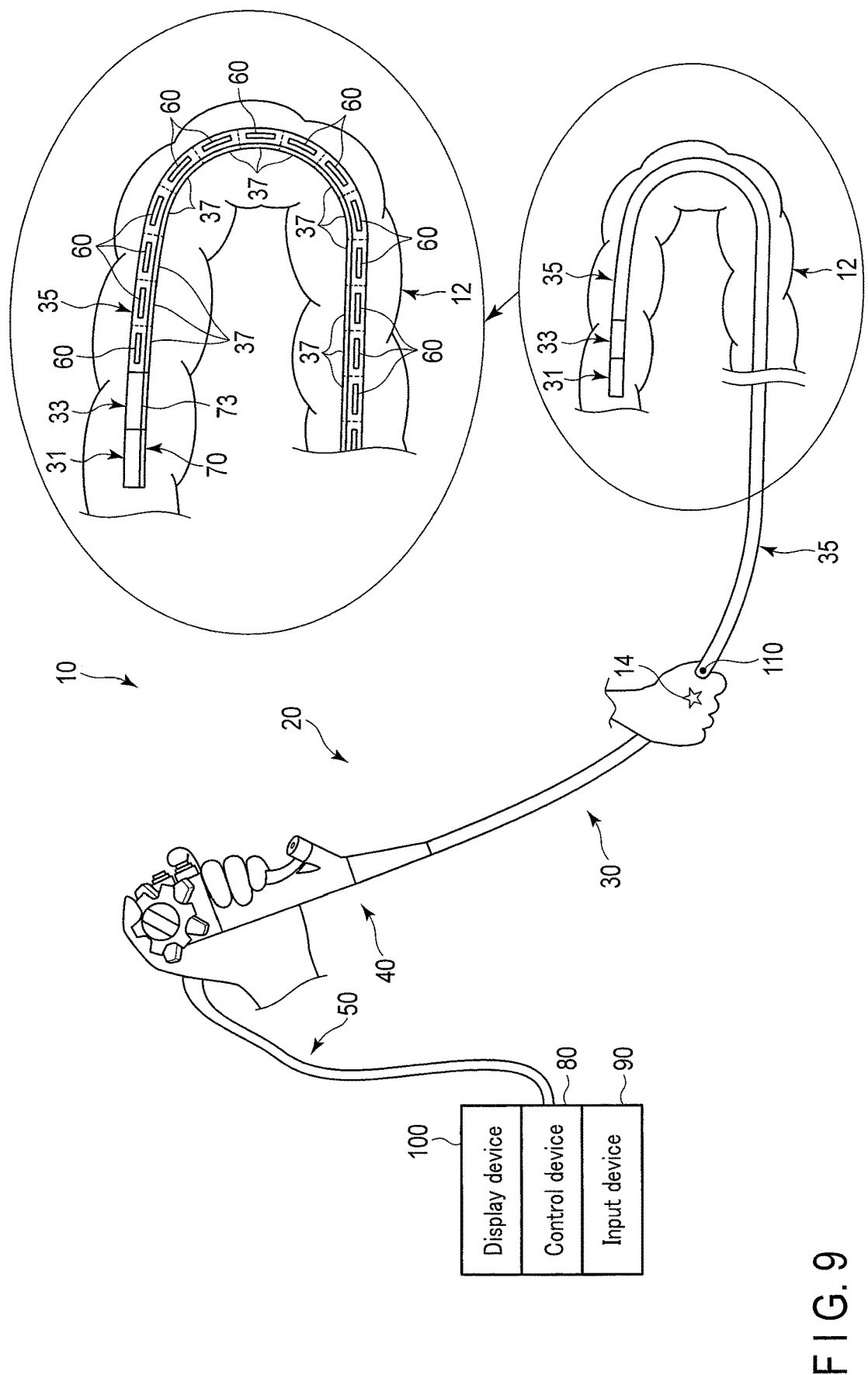
FIG. 9 is a schematic diagram of a flexible tube insertion apparatus according to a second embodiment of the present invention.

As shown in FIG. 9, the flexible tube 35 is divided into segments 37 arranged in series along the central axis direction of the insertion section 30. The segments 37 are present over the entire length of the flexible tube 35, for example. The segments 37 may be present in part of the flexible tube 35, for example. The segments 37 are changeable in bending stiffness independently of one another under control of the control device 80. Accordingly, the flexible tube 35 is partially changeable in bending stiffness because of the bending stiffnesses of the segments 37, each of which is independently controlled by the control device 80. The segments 37 may function as non-existent virtual regions, or may function as existent structures. The segments 37 may be the same or different in length. For example, in the insertion section 30, the length of a part to be inserted into a subject depends on the subject. Therefore, a part to be inserted may be divided into the segments 37, whereas a part that is arranged outside a subject and is not to be inserted into the subject may be regarded as one segment 37.

As shown in FIGS. 9 and 10, the insertion apparatus 10 includes one or more variable stiffness portions 60 that have the stiffnesses that are changeable under control of the control device 80 and change the bending stiffness of the flexible tube 35 by the stiffnesses. According to the present embodiment, the variable stiffness portions 60 changes the stiffness of the flexible tube 35 in the insertion section 30 on a segment-by-segment basis. Therefore, the following description assumes that the variable stiffness portions 60 are incorporated in the segments 37, respectively, over the entire length of the flexible tube 35. The variable stiffness portions 60 are only required to be arranged in a site of the flexible tube 35, the site being inserted into the tube portion 12 and being required to change the bending stiffness. The variable stiffness portions 60 may be incorporated in only some of the segments 37. For clarification of the illustration, FIG. 10 illustrates only one variable stiffness portion 60.

Areas in which the variable stiffness portions 60 are provided may function at least as the segments 37, respectively. A single variable stiffness portion 60 may be incorporated into the segments 37. The variable stiffness portions 60 may be arranged in a line along the central axis direction of the insertion section 30, or may be arranged in lines. If the variable stiffness portions 60 are arranged in lines, the variable stiffness portions 60 may be provided at the same position in such a manner that the variable stiffness portions 60 are adjacent to each other in the circumferential direction of the flexible tube 35, or may be provided so as to be shifted in the central axis direction of the insertion section 30.

Although not shown, the variable stiffness portions 60 are configured by an actuator including, for example, a coil pipe formed by a metal line and a conductive electroactive polymer artificial muscle (hereinafter referred to as EPAM) sealed inside the coil pipe. The central axis of the coil pipe is provided so as to match the central axis of the insertion section 30, or in parallel thereto. The coil pipe includes electrodes provided on both end portions of the coil pipe.

Each of the electrodes of the variable stiffness portions 60 is connected to the control device 80 through a signal cable incorporated into the endoscope 20, and receives electric power supplied from the control device 80. When a voltage is applied to the EPAM through the electrodes, the EPAM extends and contracts along the central axis of the coil pipe. However, the EPAM is restricted from extending and contracting by the coil pipe. This changes the stiffness of each variable stiffness portion 60. The stiffness of each variable stiffness portion 60 increases as the value of the applied voltage increases. When the variable stiffness portions 60 are changed in stiffness, in accordance with this change, the segments 37 are also changed in bending stiffness. Electric power is independently supplied to each of the electrodes. Accordingly, the variable stiffness portions 60 are changed in stiffness independently of one another, and the segments 37 are also changed in bending stiffness independently of one another. In this manner, the variable stiffness portions 60 change the bending stiffness of each segment 37 according to the change in stiffness of each variable stiffness portion 60, and partially change the bending stiffness of the flexible tube 35 according to the change in bending stiffness of the segments 37.

As the variable stiffness portion 60, a shape memory alloy may be used, instead of the EPAM.

In the optical fiber 73 of the state detection section 70, it is assumed that the detection targets are arranged in the segments 37, respectively, inside the flexible tube 35. Thus, the state calculation section 81 calculates shape information of each of the segments 37 on the basis of the state information detected by the state detection section 70. The state calculation section 81 calculates a bending shape included in the shape information of the flexible tube 35 by piecing together the shape information of the respective segments 37.

As shown in FIG. 10, the insertion apparatus 10 includes a stiffness control section 89 that is arranged in the control device 80 and controls changes in the bending stiffness, which is executed by the variable stiffness portions 60. The stiffness control section 89 is configured by, for example, a hardware circuit including ASIC, etc. The stiffness control section 89 may be configured by a processor. In the case where the stiffness control section 89 is configured by a processor, the internal memory or external memory, not shown, which is accessible by the processor, stores a program code that causes the processor to function as the stiffness control section 89 when the processor is executed.

The stiffness control section 89 changes the bending stiffness of each segment 37 so as to be appropriate for the insertion of the flexible tube 35. For this, the stiffness control section 89 calculates, for example, the insertion-appropriate bending stiffness as a bending stiffness appropriate for insertion of the flexible tube 35, in accordance with shape information calculated by the state calculation section 81. The stiffness control section 89 calculates the insertion-appropriate bending stiffness of each segment 37. The insertion-appropriate bending stiffness indicates the bending stiffness by which each segment 37 is provided with the stiffness distribution appropriate for insertion of the flexible tube 35, through the variable stiffness portions 60, in accordance with the shape information. The insertion-appropriate bending stiffness indicates the bending stiffness by which the flexible tube 35 is provided with the aforementioned stiffness distribution, through the segments 37. Hereinafter, an example of the calculation of the insertion-appropriate bending stiffness in the single segment 37 will be briefly described.

For example, assume that segments 37 receive an external force from the bent portion of the large intestine. The stiffness control section 89 specifies a segment that serves as an origination (hereinafter, referred to as an originating segment) based on shape information calculated by the state calculation section 81. Among the segments 37 that have received an external force, the originating segment corresponds to, for example, the segment 37 that has the largest bending angle. In other words, among the segments 37, the originating segment corresponds to the segment 37 that has received the greatest external force and applies the largest load to large intestine wall. Herein, the segments 37 that are arranged closer to the proximal end of the flexible tube 35 than the originating segment and are formed in a mutually continuous manner are referred to as control segments. For example, the stiffness control section 89 decreases the bending stiffness of each control segment as desired through each variable stiffness portion 60. Herein, for example, the stiffness control section 89 decreases the bending stiffness of each control segment as desired so that the bending angle remains smaller than a preset threshold value. For example, the stiffness control section 89 may decrease the bending stiffness of each control segment below that of the other segments 37. This increases the bending quantity of the control segments, so that the overall insertion section takes an obtuse-angle shape. That is, the flexible tube 35 is brought in contact with the large intestine wall at the bent portion while taking an obtuse-angle shape, which results in a decreased external force that the flexible tube 35 receives from the large intestine wall. In addition, when the bending stiffness of each control segment is decreased, the originating segment may separate from the large intestine wall. Thus, even if the insertion force that inserts the insertion section 30 toward a deep portion is applied to the insertion section 30, the insertion force is not converted into a force that pushes up the large intestine wall, but is utilized as a driving force that drives the distal end of the insertion section 30 toward a deep portion. Accordingly, the insertion section 30 easily passes through the bent portion of the large intestine. In view of the above, the insertion-appropriate bending stiffness indicates the bending stiffness with which the insertability can be improved, and which is smaller than the bending stiffness at the time when the flexible tube 35 receives an external force. The insertion-appropriate bending stiffness may be lower than the bending stiffness at the time when the shape information is input to the stiffness control section 89. The control segments may be continuous to the originating segment or may be separated from the originating segment by the predetermined number of segments 37. The control segments may correspond to all the segments 37 including the originating segment.

The stiffness control section 89 inputs, as the characteristic information to the characteristic information input section 91, the bending stiffness K as a calculated value of the insertion-appropriate bending stiffness of every segment 37. As described above, in the present embodiment, the bending stiffness K in the characteristic information is not a known value but is a calculated value that is calculated by the stiffness control section 89. The bending stiffness K is a value calculated in real time.

When the stiffness control section 89 changes the bending stiffness of the flexible tube 35 on a segment 37-by-segment 37 basis, the input device 90 inputs a control start instruction to the stiffness control section 89. Next, the stiffness control section 89 calculates the insertion-appropriate bending stiffness in accordance with a shape of the bent portion 12, in detail, the shape information calculated by the state calculation section 81. The stiffness control section 89 drives the variable stiffness portions 60 in a manner to turn the bending stiffness of the segments 37 into the insertion-appropriate bending stiffness. When the variable stiffness portions 60 changes the variable stiffness portions 60 in stiffness, the bending stiffness of the segments 37 is turned into the insertion-appropriate bending stiffness. The insertion-appropriate bending stiffness corresponds to not only the improvement in insertability, but also the magnitude of the load that the flexible tube 35 applies to the large intestine wall.

Therefore, even if the insertion force is applied to the insertion section 30, the insertion force is not converted into a force that pushes up the large intestine wall, but is utilized as a driving force. This allows the flexible tube 35 to pass through the bent portion and improves the insertability of the insertion section 30 including the flexible tube 35. In addition, the large intestine wall is not pushed up with an insertion force, so that the flexible tube 35 can reduce a patient's distress without unintentionally giving any excessive load to the large intestine wall.

The insertion of the flexible tube 35 into a deep portion is carried out when the stiffness control section 89 performs a control operation. In general, the variation in control of the bending stiffness may be caused between the segments 37, in accordance with a minimal time lag caused when the control start instruction is transmitted from the input device 90 to the respective variable stiffness portions 60 or a difference in performance between the variable stiffness portions 60. Therefore, when the flexible tube 35 passes through the bent portion, the control of the bending stiffness does not make it in time due to the variation, so that in some cases, the flexible tube 35 passes through the bent portion while having the high bending stiffness. In such cases, the insertion force (speed) at the distal end of the flexible tube 35 is decreased, so that an operator may inevitably give an excessive insertion force from the hand side to the flexible tube 35. Then, the large intestine wall is pushed up with the excessive insertion force and unintentionally, the flexible tube 35 applies an excessive load to the large intestine wall, thereby causing patient distress.

However, in the present embodiment, the insertion state calculation section 85 calculates the calculation insertion force F3, for example, based on the shape information calculated for each segment 37 by the state calculation section 81, the bending stiffness calculated for each segment 37 by the stiffness control section 89, and the distal end operation state. That is, the insertion state calculation section 85 calculates the calculation insertion force F3 even if the variation in control of the bending stiffness is caused between the segments 37 in accordance with a time lag or a performance difference.

Therefore, even if the variation is caused, in an insertion operation in progress, an operator visually observes the index 18A indicative of the calculation insertion force F3, the index 18B indicative of the measurement insertion force F4, and the appropriate range 16, all of which are display contents displayed on the display device 100, and determines whether the measurement insertion force F4 is insufficient, excessive, or appropriate. Accordingly, an operator visually observes the support information and adjusts the measurement insertion force F4 based on the support information. As described above, the insertion apparatus 10 according to the present embodiment enables the insertion of the flexible tube 35 into a deep portion inside the tube portion 12 to be safely supported based on the support information, even if a variation is caused.

The present invention is not limited to the above-described embodiment and can be embodied in practice by modifying the structural elements without departing from the gist of the invention. In addition, various inventions can be made by suitably combining the structural elements disclosed in connection with the above embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
   a flexible tube configured to be inserted into a subject;
   a first sensor configured to detect state information regarding a bending state of the flexible tube;
   a second sensor configured to measure a measurement insertion state indicative of an actual operation state of the flexible tube at a specific point that is a predetermined point closer to a proximal end than a distal end of the flexible tube; and
   a processor configured to:
      calculate, based on the state information, shape information regarding a shape of the flexible tube along a central axis direction of the flexible tube;
      input known characteristic information regarding a characteristic of the flexible tube, wherein the known characteristic information comprises a viscous resistance and a friction coefficient between the subject and the flexible tube;
      calculate, based on the known characteristic information, a distal end operation state including insertion force or speed at the distal end of the flexible tube;
      calculate a calculation insertion state indicative of an insertion state of the flexible tube at the specific point based on the shape information, the known characteristic information, and the distal end operation state; and
      calculate a difference between the calculation insertion state and the measurement insertion state; and
   a display configured to display at least the difference.

2. The flexible tube insertion apparatus according to claim 1,
   wherein the display is configured to display the calculation insertion state, the measurement insertion state, and a predetermined range that indicates whether the measurement insertion state is appropriate with respect to the calculation insertion state.

3. The flexible tube insertion apparatus according to claim 2,
   wherein the display is configured to:
      display the measurement insertion state at a display position that changes with respect to the calculation insertion state based on the difference; and
      display whether the measurement insertion state is insufficient or excessive relative to the calculation insertion state, and whether the measurement insertion state falls within the predetermined range or outside the predetermined range.

4. The flexible tube insertion apparatus according to claim 3,
   wherein the known characteristic information comprises the viscous resistance, a bending stiffness of the flexible tube, and the friction coefficient between the subject and the flexible tube.

5. The flexible tube insertion apparatus according to claim 3,
   wherein the second sensor is configured to be arranged in a site of the flexible tube that is gripped by an operator, or is arranged in a glove that covers a hand of the operator who grips the flexible tube, and perform measurement in a position where it is arranged, and
   wherein the second sensor comprises any one of a force sensor, a torque sensor, a strain sensor, an acceleration sensor, and a position sensor.

6. The flexible tube insertion apparatus according to claim 3, comprising:
   an actuator configured to change a bending stiffness of the flexible tube,
   wherein the processor is configured to control the actuator to change the bending stiffness of the flexible tube,
   wherein the flexible tube is divided into segments arranged in series along the central axis direction of the flexible tube,
   wherein the actuator is configured to change the bending stiffness on a segment-by-segment basis,
   wherein the processor is configured to calculate shape information of each of the segments based on the state information regarding the shape of the flexible tube along the central axis direction of the flexible tube, and
   wherein the processor is configured to calculate the bending stiffness for each of the segments based on the shape information of each of the segments, and input a calculated value of the bending stiffness, the viscous resistance and the friction coefficient between the subject and the flexible tube as the known characteristic information.

7. A method for controlling a flexible tube insertion apparatus, the flexible tube insertion apparatus comprising a flexible tube configured to be inserted into a subject, a first sensor configured to detect state information regarding a bending state of the flexible tube, a second sensor configured to measure a measurement insertion state indicative of an actual operation state of the flexible tube at a specific point that is a predetermined point closer to a proximal end than a distal end of the flexible tube, the method comprising:

calculating, based on the state information, shape information regarding a shape of the flexible tube along a central axis direction of the flexible tube;

inputting known characteristic information regarding a characteristic of the flexible tube, wherein the known characteristic information comprises a viscous resistance and a friction coefficient between the subject and the flexible tube;

calculating, based on the known characteristic information, a distal end operation state including insertion force or speed at the distal end of the flexible tube;

calculating a calculation insertion state indicative of an insertion state of the flexible tube at the specific point based on the shape information, the known characteristic information, and the distal end operation state;

calculating a difference between the calculation insertion state and the measurement insertion state; and displaying, by a display, at least the difference.

8. A non-transitory computer-readable medium storing instructions for controlling a flexible tube insertion apparatus, the flexible tube insertion apparatus comprising a flexible tube configured to be inserted into a subject, a first sensor configured to detect state information regarding a bending state of the flexible tube, a second sensor configured to measure a measurement insertion state indicative of an actual operation state of the flexible tube at a specific point that is a predetermined point closer to a proximal end than a distal end of the flexible tube, and a display, wherein the instructions cause a computer to at least perform:

calculating, based on the state information, shape information regarding a shape of the flexible tube along a central axis direction of the flexible tube;

inputting known characteristic information regarding a characteristic of the flexible tube, wherein the known characteristic information comprises a viscous resistance and a friction coefficient between the subject and the flexible tube;

calculating, based on the known characteristic information, a distal end operation state including insertion force or speed at the distal end of the flexible tube;

calculating a calculation insertion state indicative of an insertion state of the flexible tube at the specific point based on the shape information, the known characteristic information, and the distal end operation state;

calculating a difference between the calculation insertion state and the measurement insertion state; and controlling the display to display at least the difference.

\* \* \* \* \*